(12) United States Patent
Abushakra et al.

(10) Patent No.: US 11,191,742 B2
(45) Date of Patent: Dec. 7, 2021

(54) METHODS OF TREATING NEURODEGENERATIVE DISORDERS IN A PARTICULAR POPULATION

(71) Applicant: ALZHEON, INC., Framingham, MA (US)

(72) Inventors: Susan Abushakra, Framingham, MA (US); Aidan Power, Framingham, MA (US); Martin Tolar, Framingham, MA (US); John Hey, Framingham, MA (US); Jeremy Yu, Framingham, MA (US); Petr Kocis, Framingham, MA (US)

(73) Assignee: Alzheon, Inc., Framingham, MA (US)

( * ) Notice: Subject to any disclaimer, the term of this patent is extended or adjusted under 35 U.S.C. 154(b) by 0 days.

(21) Appl. No.: 15/758,405

(22) PCT Filed: Sep. 9, 2016

(86) PCT No.: PCT/US2016/051091
§ 371 (c)(1),
(2) Date: Mar. 8, 2018

(87) PCT Pub. No.: WO2017/044840
PCT Pub. Date: Mar. 16, 2017

(65) Prior Publication Data
US 2018/0250249 A1    Sep. 6, 2018

Related U.S. Application Data

(60) Provisional application No. 62/365,809, filed on Jul. 22, 2016, provisional application No. 62/302,027, (Continued)

(51) Int. Cl.
*A61K 31/185* (2006.01)
*A61P 25/28* (2006.01)

(52) U.S. Cl.
CPC ............ *A61K 31/185* (2013.01); *A61P 25/28* (2018.01)

(58) Field of Classification Search
CPC ............................. A61K 31/185; A61P 25/28
See application file for complete search history.

(56) References Cited

U.S. PATENT DOCUMENTS 5,698,155 A    12/1997   Grosswald et al.
8,748,656 B2    6/2014   Kong et al.
(Continued)

FOREIGN PATENT DOCUMENTS

CN    101578269 A    11/2009
CN    101600730 A    12/2009
(Continued)

OTHER PUBLICATIONS

Schmechel, Increased amyloid β-peptide deposition in cerebral cortex as a consequence of apolipoprotein E genotype in late-onset Alzheimer disease, Proc. Natl. Acad. Sci., 1993, 90, pp. 9649-9653. (Year: 1993).*

(Continued)

*Primary Examiner* — Savitha M Rao
*Assistant Examiner* — Andrew P Lee
(74) *Attorney, Agent, or Firm* — Cooley LLP

(57) ABSTRACT

Disclosed herein are methods for treating, ameliorating, and/or preventing Alzheimer's Disease in a specific patient population using tramiprosate, valyl-3-amino-1-propane-sulfonic acid, or a pharmaceutically acceptable salt thereof based upon a combination of APOE4 status and disease severity.

19 Claims, 8 Drawing Sheets

Related U.S. Application Data filed on Mar. 1, 2016, provisional application No. 62/290,287, filed on Feb. 2, 2016, provisional application No. 62/216,404, filed on Sep. 10, 2015.

(56) References Cited

U.S. PATENT DOCUMENTS

| | | |
|---|---|---|
| 9,499,480 B2 | 11/2016 | Kong et al. |
| 10,238,611 B2 | 3/2019 | Kong et al. |
| 10,471,029 B2 | 11/2019 | Tolar et al. |
| 10,857,109 B2 | 12/2020 | Kong et al. |
| 2005/0031651 A1 | 2/2005 | Gervais et al. |
| 2006/0079578 A1 | 4/2006 | Laurin et al. |
| 2008/0146642 A1 | 6/2008 | Kong et al. |
| 2009/0182056 A1 | 7/2009 | Laurin et al. |
| 2010/0113591 A1 | 5/2010 | Kong et al. |
| 2010/0183513 A1 | 7/2010 | Froestl et al. |
| 2010/0266505 A1 | 10/2010 | Black et al. |
| 2012/0071468 A1 | 3/2012 | John et al. |
| 2014/0220122 A1 | 8/2014 | Kong et al. |
| 2014/0328856 A1 | 11/2014 | Gelmont et al. |
| 2017/0095430 A1 | 4/2017 | Kong et al. |
| 2017/0172952 A1 | 6/2017 | Tolar et al. |

FOREIGN PATENT DOCUMENTS

| | | |
|---|---|---|
| JP | 2007-502418 | 2/2007 |
| JP | 2008-535907 A | 9/2008 |
| JP | 2010-514674 | 5/2010 |
| WO | WO-94/09155 A1 | 4/1994 |
| WO | WO-2005/060393 A2 | 7/2005 |
| WO | WO-2009/019534 A2 | 2/2009 |
| WO | WO-2012/006329 A2 | 1/2012 |
| WO | WO-2015/120233 A1 | 8/2015 |
| WO | WO 2015/143447 A2 | 9/2015 |

OTHER PUBLICATIONS

Sleegers et al., The pursuit of susceptibility genes for Alzheimer's disease: progress and prospects, Trends in Genetics, vol. 26, No. 2, 2010, pp. 84-93.

Abushakra, S. et al. Clinical Benefits of Tramiprosate in Alzheimer's Disease Are Associated with Higher Number of APOE4 Alleles: The "APOE4 Gene-Dose Effect", J Prey Alzheimers Dis. 2016;3(4):219-228.

Abushakra, S. et al. "Tramiprosate, an oral amyloid anti-aggregation agent, shows robust cognitive efficacy in APOE4/4 homozygous AD patients: efficacy and safety analyses from two Phase 3 trials", Neurobiology of Aging 2016;39:S22.

Aisen, P.S. et al. "Tramiprosate in mild-to-moderate Alzheimer's disease—a randomized, double-blind, placebo-controlled, multi-centre study (the Alphase Study)", Arch Med Sci. 2011. Feb;7(1): 102-11.

Caltagirone, C. et al. "The potential protective effect of tramiprosate (homotaurine) against Alzheimer's disease: a review", Aging Clin Exp Res. Dec. 2012;24(6):580-7.

Munzar, M. et al. "Clinical study of a urinary competitive ELISA for neural thread protein in Alzheimer disease", Neurol Clin Neurophysiol. 2002; 2002(1): 2-8.

"Bapineuzumab in Patients with Mild to Moderate Alzheimer's Disease (ApoE4 Non-Carrier): ClinicalTrials.gov Identifier: NCT00574132", ClinicalTrials.gov. Study First Received Dec. 10, 2007; 2007. 6 pages.

Wright, T. M., "Tramiprosate", Drugs of Today, 2006, 42(5):291-298.

Rahman, Atta-ur, "Homotaurine: Frontiers in Clinical Drug Research—CNS and Neurological Disorders"; Bentham Science Publishers, 5: 113. (2017).

Gauthier, S. et al. "Effect of tramiprosate in patients with mild-to-moderate Alzheimer's disease: exploratory analyses of the MRI sub-group of the Alphase study", J Nutr Health Aging; Jun. 2009;13(6):550-7.

Abushakra, S. et al. "Clinical Effects of Tramiprosate in APOE4/4 Homozygous Patents with Mild Alzheimer's Disease Suggest Disease Modification Potential"; J. Prey. Alzheimer's Dis. 2017;4(3):149-156.

Cosentino, S. et al. "APOE epsilon 4 allele predicts faster cognitive decline in mild Alzheimer's disease"; Neurology. May 6, 2008; 70(19 Pt 2):1842-9. Epub Apr. 9, 2008.

Peters, R. "Ageing and the brain"; Postgrad Med J. Feb. 2006; 82(964):84-8.

Sando, S. B. et al. "APOE epsilon 4 lowers age at onset and is a high risk factor for Alzheimer's disease; a case control study from central Norway"; BMC Neurol. Apr. 16, 2008; 8:9.

Hey, J. et al. "Analyses of Tramiprosate Phase 3 Trials Show Improvement in Cognition and Function In APOE4 Positive Alzheimer's Disease Subjects Reaching 4 Point Improvement From Placebo on ADAS-COG in Homozygous APOE4 Subjects, and Support Development of ALZ-801, A Novel Prodrug of Tramiprosate with Optimized Drug Properties", Neurodeger. Dis. 2015; 15(1):352-1969, p. 798.

\* cited by examiner

METHODS OF TREATING NEURODEGENERATIVE DISORDERS IN A PARTICULAR POPULATION

This application is a U.S. National Phase application, filed under 35 U.S.C. § 371(c), of International Application No. PCT/US2016/051091, filed Sep. 9, 2016, which claims priority to and the benefit of U.S. Provisional Application No. 62/216,404, filed Sep. 10, 2015, U.S. Provisional Application No. 62/290,287, filed Feb. 2, 2016, U.S. Provisional Application No. 62/302,027, filed Mar. 1, 2016, and U.S. Provisional Application No. 62/365,809, filed Jul. 22, 2016, the disclosure of each of which is hereby incorporated by reference herein in its entirety for all purposes.

FIELD OF THE INVENTION

The present disclosure is generally related to treatment of neurological disorders, including Alzheimer's disease (AD), and particularly AD in a specific patient population.

BACKGROUND OF THE INVENTION

AD is a progressive degenerative disease of the brain primarily associated with aging. Prevalence of AD in the United States in 2000 was close to 4.5 million. It was estimated that about one in ten individuals over 65 and nearly half of those over 85 are affected by AD. Approximately 360,000 patients will be diagnosed with AD each year in the United States alone.

Clinical presentation of AD is characterized by loss of memory, cognition, reasoning, judgment, and orientation. As the disease progresses, motor, sensory, and linguistic abilities are also affected until there is global impairment of multiple cognitive functions. These cognitive losses occur gradually and progressively, and typically lead to severe impairment and eventual death within twelve years of diagnosis.

AD is characterized by two major pathologic observations in the brain: neurofibrillary tangles and beta amyloid (or neuritic) plaques comprised predominantly of an aggregate of a peptide fragment known as beta amyloid peptide (Aβ). Individuals with AD exhibit characteristic Aβ deposits in the brain (Aβ plaques) and in cerebral blood vessels (beta amyloid angiopathy) as well as neurofibrillary tangles. Neurofibrillary tangles occur not only in AD but also in other dementia-inducing disorders.

SUMMARY OF THE INVENTION

The present disclosure is based, inter alia, on the discovery that homotaurine (3-amino-1-propanesulfonic acid (3-APS), tramiprosate, or Alzhemed™) and its valine prodrug form, ALZ-801, have stronger therapeutic effects on specific subsets of human patients. In particular these drugs show more efficacy in patients that are heterozygous for the Apolipoprotein E4 (APOE4) gene and have moderate AD; as well as in patients that are homozygous for the APOE4 gene and have mild-moderate or mild AD.

ALZ-801 (valyl-3-amino-1-propanesulfonic acid) is a novel, orally bioavailable, small-molecule prodrug of tramiprosate with improved pharmacokinetics and oral tolerability over tramiprosate, shown below:

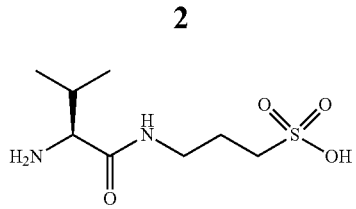

To our knowledge, nothing in the art has provided any reason to predict that an APOE4-positive patient can respond to tramiprosate or a prodrug thereof (e.g., ALZ-801) differently depending on the severity of AD. The severity of AD can be measured through the use of the Mini-mental State Examination (MMSE). As used herein, "baseline MMSE" refers to a MMSE score obtained within 60 days, preferably within 30 days, prior to initial treatment. A baseline MMSE score of 20-26 is considered to be mild AD; while a baseline MMSE score of 16-19 is considered to be moderate AD. In the present application, we subdivide moderate AD into "mild-moderate AD" defined as a baseline MMSE score of 18-19 and "more moderate AD" defined as a baseline MMSE score of 16-17. We also subdivide mild AD into "less mild AD" defined as a baseline MMSE score of 20-21 and "more mild AD" defined as a baseline MMSE score of 22-26.

Applicants have surprisingly discovered based on clinical data, that APOE4-heterozygous patients suffering from moderate AD respond unexpectedly better to treatment with tramiprosate or a prodrug thereof (e.g., ALZ-801) than the other AD patients (e.g., APOE4 negative/moderate AD; APOE4 heterozygous with mild AD). Accordingly, the present disclosure provides a novel method of treating AD in an APOE4-heterozygous patient that has moderate AD.

In addition, Applicants have surprisingly discovered based on clinical data, that APOE4/4 homozygous patients suffering from mild AD or mild-moderate AD respond unexpectedly better to treatment with tramiprosate or a prodrug thereof (e.g., ALZ-801) than the other AD patients (e.g., APOE4/4 homozygous patients with more moderate AD). In particular, APOE4/4 homozygous patients with mild AD (baseline MMSE score of 20-26) and mild-moderate AD (baseline MMSE score of 18-19) tend to show a higher improvement on tramiprosate at 150 mg BID than those with MMSE <18 at baseline. Additionally, ApoE4/4 homozygous patients with baseline MMSE ≥22 showed the highest efficacy and a progressive increase in cognitive benefit compared to placebo over the 78 weeks of the study. The same is expected for the equivalent dose (265 mg BID) of ALZ-801—a tramiprosate prodrug.

Accordingly, some aspects of the present disclosure relate to a method of treating AD in a subject, the method comprising the following steps: (i) determining the APOE4 status of the subject; (ii) determining the severity of AD in the subject; and (iii) administering, to the subject, a pharmaceutical composition capable of delivering tramiprosate to the recipient (e.g., a composition comprising tramiprosate or a prodrug thereof (e.g., ALZ-801 or a pharmaceutically acceptable salt thereof)) when the subject is determined to be APOE4 heterozygous and have moderate AD; or when the subject is determined to be APOE4/4 homozygous and have mild or mild-moderate AD.

In some embodiments, the disclosure provides a method of treating Alzheimer's Disease in a subject, the method comprising administering a pharmaceutical composition comprising valyl-3-amino-1-propanesulfonic acid or a pharmaceutically acceptable salt thereof to a subject determined to (i) be APOE4 heterozygous and have moderate Alzheimer's Disease; or (ii) be APOE4/4 homozygous and have mild or mild-moderate Alzheimer's disease.

In a related embodiment, the disclosure provides a method of treating Alzheimer's Disease in a subject, the method comprising the steps of:

a. administering a pharmaceutical composition comprising tramiprosate, valyl-3-amino-1-propanesulfonic acid or a pharmaceutically acceptable salt of either of the foregoing to a subject determined to (i) be APOE4 heterozygous and have moderate Alzheimer's Disease; or (ii) be APOE4/4 homozygous and have mild or mild-moderate Alzheimer's disease; and b. not administering, to the subject, the pharmaceutical composition when the subject is determined to be (i) APOE4 negative; (ii) APOE4 heterozygous and not suffering from moderate Alzheimer's Disease; or (iii) APOE4/4 homozygous and not suffering from mild or mild-moderate Alzheimer's disease. In one aspect of these embodiments, when the subject is determined to be (i) APOE4 negative; (ii) APOE4 heterozygous and not suffering from moderate Alzheimer's Disease; or (iii) APOE4/4 homozygous and not suffering from mild or mild-moderate Alzheimer's disease, that subject is administered a therapeutic other than tramiprosate, valyl-3-amino-1-propanesulfonic acid or a pharmaceutically acceptable salt of either of the foregoing.

In related embodiments, the disclosure provides a method of treating AD in a subject, comprising: (i) determining the APOE4 status of the subject; (ii) determining the baseline MMSE score of the subject; and (iii) administering, to the subject, a pharmaceutical composition capable of delivering tramiprosate to the recipient (e.g., a composition comprising tramiprosate or a prodrug thereof (e.g., ALZ-801 or a pharmaceutically acceptable salt thereof)) when the subject is determined to be APOE4 heterozygous and have a baseline MMSE score of 16-19; or when the subject is determined to be APOE4/4 homozygous and have a baseline MMSE score of 18-26.

The term "APOE4" status as used herein means determining the number of APOE4 alleles in the subject (e.g., 0, 1 or heterozygous, and 2 or APOE4/4 homozygous).

In some embodiments, when the subject is determined to be APOE4 negative, APOE4 heterozygous with mild AD (i.e., baseline MMSE score of 20-26, or APOE4/4 homozygous with more moderate or severe AD (i.e., baseline MMSE score of <18), the pharmaceutical composition capable of delivering tramiprosate is not administered to the subject and, optionally, the patient is treated with a different therapeutic.

In yet other related embodiments, the disclosure provides a method of treating AD in a subject, comprising: (i) receiving information about the APOE4 status and AD disease severity of the subject; and (ii) administering to the subject, a pharmaceutical composition capable of delivering tramiprosate to the recipient (e.g., a composition comprising tramiprosate or a prodrug thereof (e.g., ALZ-801 or a pharmaceutically acceptable salt thereof)) when the subject is APOE4 heterozygous and has a baseline MMSE score of 16-19; or when the subject is APOE4/4 homozygous and has a baseline MMSE score of 18-26.

In still other related embodiments, the disclosure provides a method of treating AD in a subject, comprising administering to the subject, a pharmaceutical composition capable of delivering tramiprosate to the recipient (e.g., a composition comprising tramiprosate or a prodrug thereof (e.g., ALZ-801 or a pharmaceutically acceptable salt thereof)) wherein the subject is APOE4 heterozygous and has a baseline MMSE score of 16-19; or wherein the subject is APOE4/4 homozygous and has a baseline MMSE score of 18-26.

In yet another embodiment, the disclosure provides a method of determining a subject's suitability for treatment with valyl-3-amino-1-propanesulfonic acid, comprising determining the APOE4 status of the subject and the determining the severity of the subject's Alzheimer's disease, wherein if: a) the subject is APOE4 heterozygous and has moderate Alzheimer's disease; or b) the subject is APOE4/4 homozygous and has mild or mild-moderate Alzheimer's disease, then the subject is determined to be suitable for the treatment.

In a related embodiment, the disclosure provides a method of determining a subject's suitability for treatment with tramiprosate or valyl-3-amino-1-propanesulfonic acid, or a pharmaceutically acceptable salt of either of the foregoing, comprising determining the APOE4 status of the subject and the determining the severity of the subject's Alzheimer's disease, wherein if: a) the subject is APOE4 heterozygous and has moderate Alzheimer's disease; or b) the subject is APOE4/4 homozygous and has mild or mild-moderate Alzheimer's disease, then the subject is determined to be suitable for the treatment; and if (i) the subject is APOE4 heterozygous and has mild Alzheimer's disease; (ii) the subject is APOE4 negative; or (iii) the subject is APOE4/4 homozygous and has more moderate Alzheimer's disease, then the subject is determined to be unsuitable for the treatment In certain aspects of the above embodiments, the subject is treated or determined to be suitable for treatment if they are APOE4/4 homozygous and have a baseline MMSE score of 18-26, 19-26, 20-26, 21-26, or 22-26. In more specific aspects of these embodiments, the subject is treated or determined to be suitable for treatment if they are APOE4/4 homozygous and have a baseline MMSE score of 20-26. In even more specific aspects of these embodiments, the subject is treated or determined to be suitable for treatment if they are APOE4/4 homozygous and have a baseline MMSE score of 22-26.

In some embodiments, the pharmaceutical composition is administered to deliver a dose of tramiprosate in a range of 100 mg to 300 mg per dose. In some aspects of these embodiments, the pharmaceutical composition is administered to deliver a dose of tramiprosate in a range of 100 mg-150 mg/dose. In more specific aspects of these embodiments, the pharmaceutical composition is administered to deliver 150 mg/dose. In some aspects of these embodiments, the pharmaceutical composition comprises 300-350 mg of ALZ-801/dose. In more specific aspects of these embodiments, the pharmaceutical composition comprises 265 mg of ALZ-801/dose.

In some embodiments, the pharmaceutical composition is administered once daily or twice daily. In some aspects of these embodiments, the pharmaceutical composition is administered twice daily.

In some embodiments, the pharmaceutical composition is administered to the subject for a period of time, e.g. 13 weeks or more; 26 weeks or more; 52 weeks or more; 65 weeks or more; or 78 weeks or more.

It should be understood that the methods of this invention are considered effective if the decline of cognitive abilities is slowed as compared to a standard-of-care control treatment with an anticholinesterase inhibitor with or without memantine (e.g., donepezil alone or in combination with memantine). The treatment efficacy can be determined by metrics known in the art, e.g., the ADAS-Cog score or CDR-SB score. For the ADAS-Cog score or CDR-SB score, a higher score indicates lower cognition. In some embodiments, a subject diagnosed as APOE4 heterozygous and having moderate AD has an ADAS-Cog score that increases at an average rate of no more than 0.13 per week when the subject is being treated with the pharmaceutical composition over a period of between 52 and 78 weeks. In some embodiments, the subject's ADAS-Cog score increases by no more than 7 after administration for 52 weeks, as compared to subject's baseline ADAS-Cog score. In some embodiments, the subject's CDR-SB score increases at an average rate of no more than 0.05 per week when the subjected is being treated with the pharmaceutical composition over a period of between 52 and 78 weeks. In some embodiments, the subject's CDR-SB score increases no more than 3.0 after administration for 52 weeks, as compared to subject's baseline CDR-SB score.

In some embodiments, the subject is 85 years old or less, e.g., 65-85 years old.

In some embodiments, the treatment does not induce vasogenic edema.

In some embodiments, the disclosure provides a pharmaceutical composition comprising between 260 mg and 270 mg (e.g., 265 mg) of valyl-3-amino-1-propanesulfonic acid; and a pharmaceutically acceptable carrier, wherein the composition is formulated as an instant release, oral tablet or capsule.

In some embodiments, the disclosure provides a method of treating Alzheimer's disease comprising administering to a subject in need thereof, the instant release, oral, pharmaceutical composition comprising between 260 mg and 270 mg (e.g., 265 mg) of valyl-3-amino-1-propanesulfonic acid described above. In some aspects of these embodiments, the method comprised administering the composition twice a day.

BRIEF DESCRIPTION OF FIGURES

FIG. 7, panel B, demonstrates the effect of 150 mg BID tramiprosate on CDR-SB scores in APOE4/4 homozygous patients over 52, 65 and 78 weeks, broken down by various ranges of disease severity (as measured by baseline MMSE scores) as compared to a placebo control.

DETAILED DESCRIPTION OF THE INVENTION

Definitions

Figure 1:
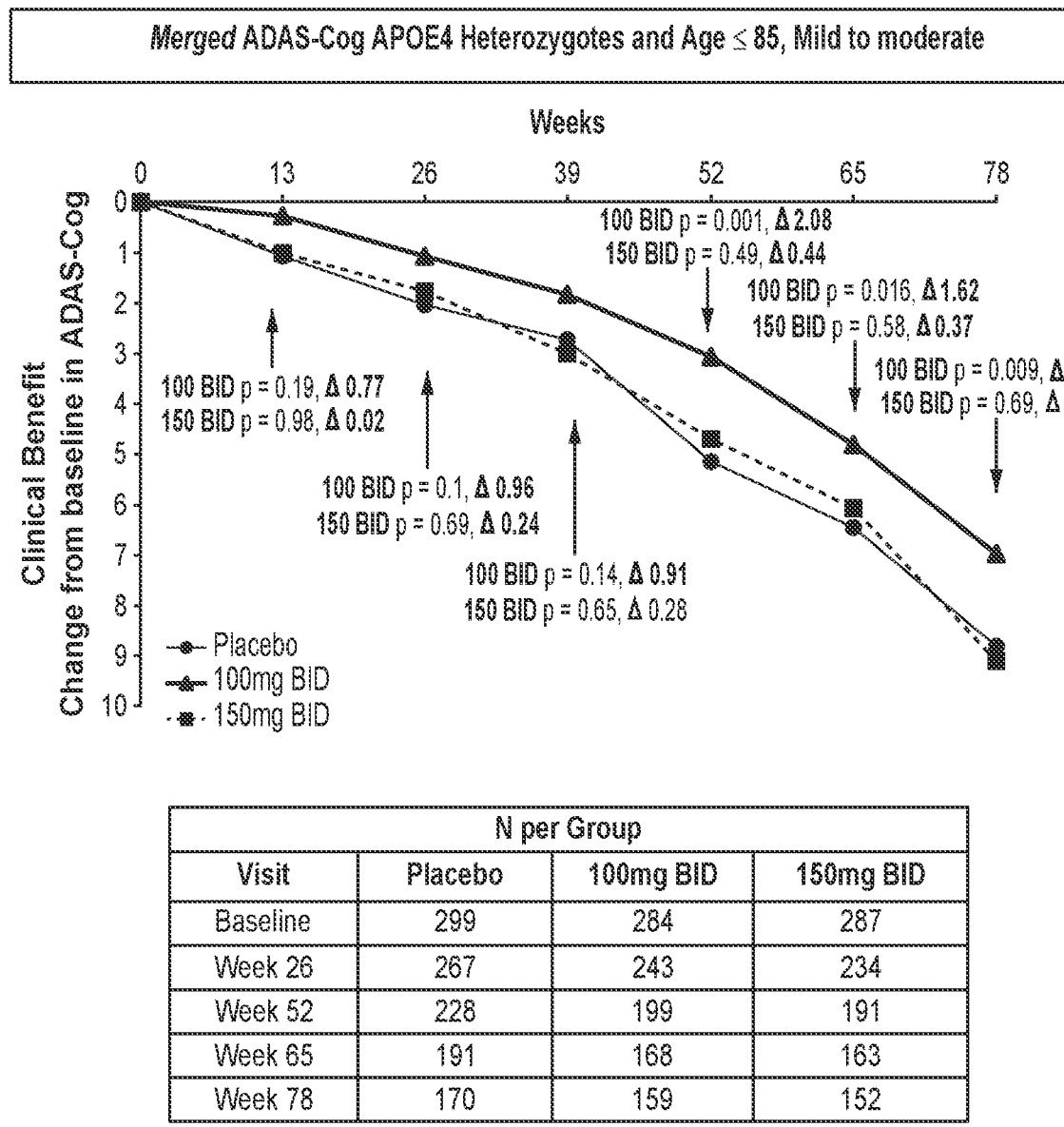
FIG. 1 demonstrates time course of tramiprosate effect (Least Square (LS) Mean) on ADAS-Cog in APOE4 Heterozygous Population at 100 mg BID and 150 mg BID (Population ≤Age 85 Years, mild to moderate AD).

The following definitions are used in connection with the disclosure.

The terms "subject" and "patient" are used interchangeably herein and refer to a human diagnosed with Alzheimer's Disease.

As used herein, the term "APOE4 positive" or "APOE4$^+$" refers to the presence of at least one APOE4 allele in a subject, e.g., one or two APOE4 alleles. In some aspects, the subject may have a single APOE4 allele, i.e., they are heterozygous for APOE4 and will be denoted as "APOE4 heterozygous" or as an "APOE4 heterozygote". In other aspects, the subject may have 2 APOE4 alleles, i.e., they are homozygous for APOE4 and will be denoted as "APOE4/4 homozygous" or as an "APOE4/4 homozygote".

As used herein, the term "APOE4 negative" refers to the absence of APOE4 allele in a subject.

As used herein, the terms "placebo" and "control" are used interchangeably to refer to Aricept® alone (i.e. donepezil) or in combination with memantine.

As used herein, an "effective amount" when used in connection with another therapeutic agent is an amount that is effective for treating or preventing a condition in combination with a compound. "In combination with" includes administration within the same composition and via separate compositions; in the latter instance, the other therapeutic agent is effective for treating or preventing a condition during a time when the compound exerts its prophylactic or therapeutic effect, or vice versa.

As used herein, the term "pharmaceutically acceptable" refers to drugs, medicaments, inert ingredients etc., which the term describes, suitable for use in contact with the tissues of humans and lower animals without undue toxicity, incompatibility, instability, irritation, allergic response, and the like, commensurate with a reasonable benefit/risk ratio. It preferably refers to a compound or composition that is approved or approvable by a regulatory agency of the Federal or state government or listed in the U.S. Pharmacopoeia or other generally recognized pharmacopoeia for use in animals and more particularly in humans.

As used herein, the term "pharmaceutical composition" refers to at least one compound and at least one pharmaceutically acceptable vehicle, with which the compound is administered to a patient.

The term "carrier" refers to diluents or fillers, disintegrants, precipitation inhibitors, surfactants, glidants, binders, lubricants, anti-oxidants, and other excipients and vehicles with which the compound is administered. Carriers are generally described herein and also in "Remington's Pharmaceutical Sciences" by E. W. Martin. Examples of carriers include, but are not limited to, aluminum monostearate, aluminum stearate, carboxymethylcellulose, carboxymethylcellulose sodium, crospovidone, glyceryl isostearate, glyceryl monostearate, hydroxyethyl cellulose, hydroxyethyl cellulose, hydroxymethyl cellulose, hydroxyoctacosanyl hydroxystearate, hydroxypropyl cellulose, hydroxypropyl cellulose, hydroxypropyl methylcellulose, lactose, lactose monohydrate, magnesium stearate, mannitol, microcrystalline cellulose, poloxamer 124, poloxamer 181, poloxamer 182, poloxamer 188, poloxamer 237, poloxamer 407, povidone, silicon dioxide, colloidal silicon dioxide, silicone, silicone adhesive 4102, and silicone emulsion. It should be understood, however, that the carriers selected for the pharmaceutical compositions provided in the present disclosure, and the amounts of such carriers in the composition, may vary depending on the method of formulation (e.g., dry granulation formulation, solid dispersion formulation).

The term "diluent" or "filler" generally refers to a substance that is used to dilute the compound of interest prior to delivery. Diluents can also serve to stabilize compounds. Examples of diluents may include starch, saccharides, disaccharides, sucrose, lactose, polysaccharides, cellulose, cellulose ethers, hydroxypropyl cellulose, sugar alcohols, xylitol, sorbitol, maltitol, microcrystalline cellulose, calcium or sodium carbonate, lactose, lactose monohydrate, dicalcium phosphate, cellulose, compressible sugars, dibasic calcium phosphate dehydrate, mannitol, microcrystalline cellulose, and tribasic calcium phosphate.

The term "disintegrant" generally refers to a substance which, upon addition to a solid preparation, facilitates its break-up or disintegration after administration and permits the release of an active ingredient as efficiently as possible to allow for its rapid dissolution. Examples of disintegrants may include maize starch, sodium starch glycolate, croscarmellose sodium, crospovidone, microcrystalline cellulose, modified corn starch, sodium carboxymethyl starch, povidone, pregelatinized starch, and alginic acid.

The term "precipitation inhibitors" generally refers to a substance that prevents or inhibits precipitation of the active agent. One example of a precipitation inhibitor includes hydroxypropyl methylcellulose.

The term "surfactants" generally refers to compounds that lower the surface tension between two liquids or between a liquid and a solid. Examples of surfactants include poloxamer and sodium lauryl sulfate.

The term "glidant" generally refers to substances used in tablet and capsule formulations to improve flow-properties during tablet compression and to produce an anti-caking effect. Examples of glidants may include colloidal silicon dioxide, talc, fumed silica, starch, starch derivatives, and bentonite.

The term "binder" generally refers to any pharmaceutically acceptable film which can be used to bind together the active and inert components of the carrier together to maintain cohesive and discrete portions. Examples of binders may include hydroxypropyl cellulose, hydroxypropyl methylcellulose, povidone, copovidone, ethyl cellulose, gelatin, and polyethylene glycol.

The term "lubricant" generally refers to a substance that is added to a powder blend to prevent the compacted powder mass from sticking to the equipment during the tableting or encapsulation process. A lubricant can aid the ejection of the tablet form the dies, and can improve powder flow. Examples of lubricants may include magnesium stearate, stearic acid, silica, fats, calcium stearate, polyethylene glycol, sodium stearyl fumarate, or talc; and solubilizers such as fatty acids including lauric acid, oleic acid, and $C_8/C_{10}$ fatty acid.

As used herein, the term "pharmaceutically acceptable salt," as used herein unless otherwise defined, is a salt of a basic group, such as an amino group, or of an acidic group, such as a carboxyl group, on the compounds disclosed herein. Illustrative salts of a basic group include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, and pamoate (i.e., 1,1'-methylene-bis-(2-hydroxy-3-naphthoate)) salts. Illustrative salts of an acidic group include, but are not limited, to lithium, sodium, potassium, calcium, magnesium, aluminum, chromium, iron, copper, zinc, cadmium, ammonium, guanidinium, pyridinium, and organic ammonium salts.

As used herein, the term "treating" or "treatment" of any disease or disorder refers, in some embodiments, to ameliorating at least one disease or disorder (i.e., arresting or reducing the development of the disease or at least one of the clinical symptoms thereof). In certain embodiments "treating" or "treatment" refers to ameliorating at least one physical parameter, which may or may not be discernible by the patient. In certain embodiments, "treating" or "treatment" refers to inhibiting the disease or disorder, either physically, (e.g., stabilization of a discernible symptom), physiologically, (e.g., stabilization of a physical parameter), or both. In certain embodiments, "treating" or "treatment" refers to delaying the onset of certain symptoms of the disease or disorder. The term "treating" refers to any indicia of success in the treatment or amelioration of an injury, pathology or condition, including any objective or subjective parameter such as abatement; remission; diminishing of symptoms or making the injury, pathology or condition more tolerable to the subject; slowing in the rate of degeneration or decline; making the final point of degeneration less debilitating; improving a subject's physical or mental well-being; or, in some situations, preventing the onset of dementia. The treatment or amelioration of symptoms can be based on objective or subjective parameters; including the results of a physical examination, a psychiatric evaluation, or a cognition test such as the Clinical Dementia Rating (CDR) scale, Mini-mental State Examination (MMSE), Disability Assessment for Dementia (DAD), Alzheimer's Disease Assessment Scale-Cognitive Subscale (ADAS-Cog), or another test known in the art. For example, the methods of the invention successfully treat a subject's dementia by slowing the rate of or lessening the extent of cognitive decline.

As used herein, the term "bioequivalence" refers to equivalence of the rate and extent of absorption of a drug after administration of equal doses of the drug or prodrug to a patient.

As used herein, the term "statistically significant" refers to means that an observation or an event is not attributed to random chance, $p=0.05$ or less.

The term "baseline score" and forms thereof, such as "baseline MMSE", "baseline ADAS-Cog score" and "baseline CDR-SB score," as used herein refer to a subject's score in a particular test obtained 0-60 days, preferably 0-30 days, prior the treatment for which efficacy is to be determined (or prior to treatment with a corresponding placebo or control).

As used herein, "mildly severe AD" and "mild AD" are used interchangeably and refer to a baseline MMSE score of 20-26; "less mildly severe AD" and "less mild AD" are used interchangeably and refer to a baseline MMSE score of 20-21; and "more mildly severe AD" and "more mild AD" are used interchangeably and refer to a baseline MMSE score of 22-26.

As used herein, "moderately severe AD" and "moderate AD" are used interchangeably and refer to a baseline MMSE score of 16-19; "mild-moderately severe AD" and "mild moderate AD" are used interchangeably and refer to a baseline MMSE score of 18-19; and "more moderately severe AD" and "more moderate AD" are used interchangeably and refer to a baseline MMSE score of 16-17.

The term "about" when used in connection with a referenced numeric indication means the referenced numeric indication plus or minus up to 10% of that referenced numeric indication. For example, the language "about 100" covers the range of 90 to 110.

Methods for Treating AD

Individuals presently suffering from AD can be recognized from characteristic dementia, as well as the presence of risk factors described below. In addition, a number of diagnostic tests based on cognitive and neurological testing are available for identifying individuals who have AD. For example, individuals suffering from AD can be diagnosed by the CDR scale, MMSE, ADAS-Cog, or any other test known in the art, as discussed herein. Baseline scores on suitable metrics including the MMSE and the ADAS together with other metrics designed to evaluate a more normal population can be used to find an at-risk population. Higher values for ADAS-Cog, CDR-SB and NPI indicate greater severity, while lower values in DAD and MMSE indicate greater severity.

Another method for identifying an at-risk group utilizes an assay for neural thread protein in the urine; see, e.g., Munzar et al., *Neurology and Clinical Neurophysiology*, Vol. 2002, No. 1. Patients with high risk for AD can also be selected from a population by screening for early signs of memory loss or other difficulties associated with pre-Alzheimer's symptomatology, a family history of AD, patients with Mild Cognitive Impairment (MCI), genetic risk factors, age, sex, and other features found to predict high-risk for AD. In addition, AD can be diagnosed through imaging techniques, e.g., the use of β-amyloid imaging agents (e.g., florbetaben, florbetapir or flutemetamol).

The APOE4 (i.e., APOE ε4) allele of apolipoprotein E gene is the strongest genetic risk factor for patients with late-onset AD. APOE4$^+$ subjects with at least one APOE ε4 allele account for 50%-60% of AD cases vs. 25% prevalence in healthy individuals. APOE4$^+$ AD patients present with decreased age of onset, increased severity and accelerated progression of AD. Subjects with two APOE ε4 alleles account for 10%-14% of AD and exhibit an even more aggressive disease progression. APOE ε4 allele leads to an increased brain AP deposition, increased CSF tau and p-tau, and faster cognitive decline. In addition, demented patients carrying one or two APOE ε4 alleles are more likely to have AD, resulting in significantly reduced rate of disease misdiagnosis in clinical studies (2% vs. 42% in non-APOE4 patients).

Methods of identifying APOE4-postive patients are known in the art and can be performed by any approach capable of determining that a patient as having one or two copies of the ε4 allele. In some embodiments, sequencing technology is used to determine the presence and/or number of APOE4 alleles. Methods of determining the severity of AD can be based on the CDR scale, MMSE, ADAS-Cog, or any other test known in the art.

Analysis of data from clinical studies based on tramiprosate revealed a specific responsive patient population: subjects with moderate AD who are APOE4 positive. For example, as shown in Tables 1 and 2, in all APOE4$^+$ patients (i.e., including both homozygotes and heterozygotes) under 85 years old, the patients with moderate AD are found to be more responsive to tramiprosate than the patients with mild AD, as indicated by a larger positive delta value in the moderate group over the mild group. Similarly, as shown in Tables 3 and 4, in heterozygous APOE4$^+$ patients under 85 years old, the patients with moderate AD are found to be more responsive to tramiprosate than the patients with mild AD. The delta value in all of these tables is calculated by measuring the increase in score over baseline for each patient in a treatment group and obtaining the mean increase for such group and then subtracting that value from the mean increase in score over baseline for all patients in the placebo group. Thus, a positive delta value in these tables represents an improvement over the placebo group.

In some embodiments, the subject is determined to have moderate AD when the subject has a baseline MMSE score in the range of 16-19. In some embodiments, the subject is determined to have mild AD when the subject has a baseline MMSE score in the range of 20-26. Tramiprosate also showed a favorable safety profile: the most common adverse event was nausea. Safety data from Phase 3 tramiprosate studies support bridging to the ALZ-801 safety database, based on bioequivalence. The disclosures in provisional application Ser. No. 62/216,404, filed Sep. 10, 2015, 62/290,287, filed Feb. 2, 2016, and 62/365,809, filed Jul. 22, 2016 are incorporated herein for all purposes and particularly regarding dosages and formulations.

Accordingly, in one aspect, the present disclosure relates to a method of treating AD in a subject based on the determination of APOE4 phenotype and AD severity in the subject. In some embodiments, the invention provides a method that comprises the following steps: (i) determining the presence or absence of an APOE4 allele in the subject; (ii) determining the severity of AD in the subject; and (iii) administering, to the subject, a pharmaceutical composition comprising ALZ-801 or a pharmaceutically acceptable salt thereof when the subject is determined to be APOE4 positive and have moderate AD.

In certain aspects, when the subject is tested APOE4 negative, the pharmaceutical composition that delivers tramiprosate to the recipient (e.g. a composition comprising tramiprosate, ALZ-801 or a pharmaceutically acceptable salt thereof) may not be administered to the subject. In other aspects, when the severity of AD in the subject is determined to be not moderate, the pharmaceutical composition that delivers tramiprosate to the recipient may not be administered to the subject. For example, when the subject has mild AD, the pharmaceutical composition that delivers tramiprosate to the recipient may not be administered to the subject.

In certain aspects, the pharmaceutical composition that delivers tramiprosate to the recipient comprises ALZ-801. In alternate aspects, the pharmaceutical composition that delivers tramiprosate to the recipient comprises tramiprosate.

In some embodiments, when the subject is tested APOE4 negative or the severity of AD in the subject is not moderate (e.g., mild), a therapy other than tramiprosate, ALZ-801 or a pharmaceutically acceptable salt thereof or tramiprosate may be administered to the subject.

In one aspect, the present disclosure relates to a method of treating Alzheimer's disease comprising the steps of: (i) receiving information related to the presence or absence of an APOE4 allele in a human patient suffering from Alzheimer's disease; (ii) receiving information related to the severity of the Alzheimer's disease in the human patient; and (iii) administering to the patient in need thereof tramiprosate, ALZ-801 or a pharmaceutically acceptable salt thereof when the information indicates that the patient has at least one APOE4 allele and has moderate severity of Alzheimer's disease.

In yet another aspect, the present disclosure also relates to a method of predicting a subject's responsiveness to tramiprosate, ALZ-801 or a pharmaceutically acceptable salt thereof, the method comprising: (i) determining the presence or absence of an APOE4 allele in the subject; (ii) determining the severity of AD in the subject; and (iii) identifying the subject as being responsive to tramiprosate, ALZ-801 or a pharmaceutically acceptable salt thereof when the subject is determined to be APOE4 positive and have moderate AD.

In a further aspect, the present disclosure relates to a method of predicting the efficacy of tramiprosate, ALZ-801 or a pharmaceutically acceptable salt thereof in the treatment of a human patient suffering from Alzheimer's disease comprising the steps of: (i) determining the presence or absence of an APOE4 allele in the patient; and (ii) determining the severity of the patient's Alzheimer disease, wherein the presence of at least one APOE4 allele and a determination that the patient has moderately severe Alzheimer's disease is predictive of the efficacy of tramiprosate, ALZ-801 or a pharmaceutically acceptable salt thereof in the treatment.

The treatment efficacy of the pharmaceutical composition disclosed herein can be assessed using tests known in the art, such as ADAS-Cog, the CDR scale, MIVISE, DAD, or combinations thereof.

In certain embodiments, the treatment efficacy may be determined through the ADAS-Cog scale. ADAS was designed to measure the severity of the most important symptoms of AD. Its subscale ADAS-Cog is the most popular cognitive testing instrument used in clinical trials of nootropics. It consists of 11 tasks measuring the disturbances of memory, language, praxis, attention and other cognitive abilities which are often referred to as the core symptoms of AD. The ADAS-Cog scale helps evaluate cognition and differentiates between normal cognitive functioning and impaired cognitive functioning. It is especially useful for determining the extent of cognitive decline and can help evaluate which stage of AD a person is in, based on his answers and score. The ADAS-Cog scale can be used in clinical trials in order to determine incremental improvements or declines in cognitive functioning.

In some embodiments, the treatment is considered to be effective when the subject's ADAS-Cog score increases at an average rate of no more than 0.13 per week when the subjected is being treated with the pharmaceutical composition over a period of between 52 and 78 weeks (e.g., 52 weeks, 65 weeks, or 78 weeks). In some embodiments, the treatment is considered to be effective when the subject's ADAS-Cog score increases at an average rate of no more than 0.125 per week when the subjected is being treated with the pharmaceutical composition over a period of between 52 and 78 weeks (e.g., 52 weeks, 65 weeks, or 78 weeks). In some embodiments, the treatment is considered to be effective when the subject's ADAS-Cog score increases at an average rate of no more than 0.12 per week when the subjected is being treated with the pharmaceutical composition over a period of between 52 and 78 weeks (e.g., 52 weeks, 65 weeks, or 78 weeks). In some embodiments, the treatment is considered to be effective when the subject's ADAS-Cog score increases at an average rate of no more than 0.115 per week when the subjected is being treated with the pharmaceutical composition over a period of between 52 and 78 weeks (e.g., 52 weeks, 65 weeks, or 78 weeks). In some embodiments, the treatment is considered to be effective when the subject's ADAS-Cog score increases at an average rate of no more than 0.11 per week when the subjected is being treated with the pharmaceutical composition over a period of between 52 and 78 weeks (e.g., 52 weeks, 65 weeks, or 78 weeks).

In some embodiments, the treatment is considered to be effective when the subject's ADAS-Cog score increases by less than about 1.0, less than about 2.0, less than about 3.0, less than 4.0, less than 5.0, or less than 6.0 after administration for 52 weeks as compared to the subject's baseline ADAS-Cog score. In some embodiments, the treatment is considered to be effective when the subject's ADAS-Cog score increases in the range of about 0-6.0, 0-5.0, 0-4.0, 0-3.0, 0.5-6.0, 0.5-5.0, 0.5-4.0, 0.5-3.0, 1.0-6.0, 1.0-5.0, 1.0-4.0, or 1.0-3.0 after administration for 52 weeks as compared to the subject's baseline ADAS-Cog score.

In some embodiments, the treatment is considered to be effective when the subject's ADAS-Cog score increases by less than about 3.0, less than about 4.0, less than about 5.0, less than about 6.0, less than about 7.0, or less than about 8.0 after administration for 65 weeks as compared to the subject's baseline ADAS-Cog score. In some embodiments, the subject's ADAS-Cog score increases in the range of about 0-8.0, 1.0-7.0, 2.0-6.0, or 3.0-6.0 after administration for 65 weeks as compared to the subject's baseline ADAS-Cog score.

In some embodiments, the subject's ADAS-Cog score increases by less than about 5.0, less than about 6.0, less than about 7.0, less than about 8.0, less than about 9.0, or less than about 10.0 after administration for 78 weeks as compared to the subject's baseline ADAS-Cog score. In some embodiments, the subject's ADAS-Cog score increases in the range of about 0-10.0, 1.0-9.0, 2.0-9.0, 3.0-9.0, or 4.0-9.0 after administration for 78 weeks as compared to the subject's baseline ADAS-Cog score.

In some embodiments, a placebo can be used to determine treatment efficacy. Specifically, the difference in ADAS-Cog score between a test patient receiving the pharmaceutical composition and the average ADAS-Cog score determined in a group of patients receiving the placebo (the "placebo group") can be used to determine treatment efficacy. It should be understood that the placebo group is a group wherein each patient received standard dosing and dosages of Aricept® alone (i.e. donepezil) or together with memantine. A patient having a statistically significantly lower ADAS-Cog score than the placebo group means that the treatment is effective. Similarly, a patient whose increase in ADAS-Cog score after a period of treatment as compared to their baseline ADAS-Cog score is statistically significantly less than the average increase in ADAS-Cog score of the placebo group after the same time period, means that the treatment is effective.

In some embodiments, the treatment is considered to be effective when the change in the subject's baseline ADAS-Cog score is at least about 2.5, at least about 3.0, at least about 3.5, at least about 3.75, at least about 4.0, or at least about 4.25 less after administration for 52 weeks as compared to the average change in baseline ADAS-Cog score in the placebo group.

In some embodiments, the treatment is considered to be effective when the change in the subject's baseline ADAS-Cog score is at least about 2.5, at least about 3.0, at least about 3.5, at least about 3.75, at least about 4.0, or at least about 4.25 less after administration for 65 weeks as compared to the average change in baseline ADAS-Cog score in the placebo group.

In some embodiments, the treatment is considered to be effective when the change in the subject's baseline ADAS-Cog score is at least about 2.5, at least about 3.0, at least about 3.5, at least about 3.75, at least about 4.0, or at least about 4.25 less after administration for 78 weeks as compared to the average change in baseline ADAS-Cog score in the placebo group.

A CDR-SB score can also be used to quantify treatment efficacy. In some embodiments, the treatment is considered to be effective when the subject's CDR-SB score increases at an average rate of no more than 0.055 per week when the subject is being treated with the pharmaceutical composition over a period of between 52 and 78 weeks (e.g., 52 weeks, 65 weeks or 78 weeks). In some embodiments, the treatment is considered to be effective when the subject's CDR-SB score increases at an average rate of no more than 0.050 per week when the subject is being treated with the pharmaceutical composition over a period of between 52 and 78 weeks (e.g., 52 weeks, 65 weeks or 78 weeks). In some embodiments, the treatment is considered to be effective when the subject's CDR-SB score increases at an average rate of no more than 0.045 per week when the subject is being treated with the pharmaceutical composition over a period of between 52 and 78 weeks (e.g., 52 weeks, 65 weeks or 78 weeks). In some embodiments, the treatment is considered to be effective when the subject's CDR-SB score increases at an average rate of no more than 0.040 per week when the subjected is being treated with the pharmaceutical composition over a period of between 52 and 78 weeks (e.g., 52 weeks, 65 weeks or 78 weeks).

In some embodiments, the subject's CDR-SB score increases no more than 3.0, no more than 2.5 or no more than 2.1 over the baseline CDR-SB score after administration for 52 weeks. In some embodiments, the subject's CDR-SB score increases no more than 3.5, no more than 3.25 or no more than 3.0 over the baseline CDR-SB score after administration for 65 weeks. In some embodiments, the subject's CDR-SB score increases no more than 4.5, no more than 4.0 or no more than 3.5 over the baseline CDR-SB score after administration for 78 weeks.

In some embodiments, the treatment does not induce vasogenic edema. APOE4$^+$ patients are at risk of vasogenic edema with amyloid antibody treatments. By providing an alternative treatment to APOE4$^+$ patients, the treatment disclosed herein can reduce the risk of vasogenic edema.

For the purposes of administration, in certain embodiments, tramiprosate, ALZ-801 or a pharmaceutically acceptable salt thereof can be administered as a raw chemical or formulated as pharmaceutical compositions. Pharmaceutical compositions useful in the present disclosure comprise tramiprosate, ALZ-801 or a pharmaceutically acceptable salt thereof, and one or more pharmaceutically acceptable carriers. Tramiprosate, ALZ-801 or a pharmaceutically acceptable salt thereof is present in the composition in an effective amount to treat AD. In some specific embodiments, tramiprosate, ALZ-801 or a pharmaceutically acceptable salt thereof is administered as a pharmaceutical composition.

Pharmaceutic compositions comprising tramiprosate, ALZ-801 or a pharmaceutically acceptable salt thereof can be administered orally. Pharmaceutical compositions comprising tramiprosate, ALZ-801 or a pharmaceutically acceptable salt thereof can also be administered by any other convenient route, for example, by intravenous infusion or bolus injection, by absorption through epithelial or mucocutaneous linings (e.g., oral mucosa, rectal and intestinal mucosa, etc.) and can be administered together with another biologically active agent. Administration can be systemic or local. Various delivery systems are known, e.g., encapsulation in liposomes, microparticles, microcapsules, capsules, etc., and can be used to administer a compound. In certain embodiments, more than one compound is administered to a subject. Methods of administration include but are not limited to intradermal, intramuscular (including depot), intraperitoneal, intravenous, subcutaneous (including depot), intranasal, epidural, oral, sublingual (including rapid dissolving tablet, gum or equivalent), intranasal, intracerebral, intravaginal, transdermal, rectally, Intrapulmonary (aerosol or equivalent, including by inhalation), or topically, particularly to the ears, nose, eyes, or skin.

In a particular embodiment, a composition comprising tramiprosate, ALZ-801 or a pharmaceutically acceptable salt thereof is administered orally in a loose-filled capsule and provides for an extended half-life. In one aspect of this embodiment, a composition comprising tramiprosate, ALZ-801 or a pharmaceutically acceptable salt thereof supplied in the loose-filled capsule provides a half-life of about 10 to about 18 hours.

In another particular embodiment, a composition comprising tramiprosate, ALZ-801 or a pharmaceutically acceptable salt thereof is administered orally in an immediate release tablet formulation. In one aspect of this embodiment, a composition comprising tramiprosate, ALZ-801 or a pharmaceutically acceptable salt thereof supplied in the immediate release table provides a half-life of 12 to about 24 hours.

In certain embodiments, the dosage range for oral administration of tramiprosate, ALZ-801 or a pharmaceutically acceptable salt thereof is generally about 0.001 mg to about 2000 mg of a compound per kg body mass. In some embodiments, the oral dose is 0.01 mg to 100 mg per kg body mass, 0.1 mg to 50 mg per kg body mass, 0.5 mg to 20 mg per kg body mass, or 1 mg to 10 mg per kg body mass. In some embodiments, the oral dose is 5 mg of a compound per kg body mass.

In further embodiments, the dose is about 10 mg to about 1000 mg, including all ranges and subranges there between, e.g., about 10 mg to about 900 mg, about 10 mg to about 500 mg, about 10 mg to about 300 mg, about 50 mg to about 300 mg, about 50 mg to about 250 mg, or about 100 mg to about 300 mg. In still further embodiments, the composition comprises tramiprosate and the dose is 100 mg or 150 mg. In some embodiments, the composition comprises ALZ-801 and the dose is about 250 mg. In some embodiments, the composition comprises ALZ-801 and the dose is about 265 mg. In some embodiments, the composition comprises ALZ-801 and the dose is about 165 mg. In some embodiments, the composition comprises ALZ-801 and the dose is about 175 mg.

In still further embodiments, ALZ-801 is formulated as an immediate release oral formulation. In other aspects, the oral formulation is a loose-filled formulation. In particular aspects of these embodiments, the ALZ-801 is administered in a dose range of 200 mg to 300 mg. For example, the dosage may be 220 mg to 280 mg; 240 mg to 270 mg, 250 mg to 270 mg, 250 mg to 280 mg, or 260 mg to 270 mg. In certain aspects, the dose is 265 mg.

A composition comprising tramiprosate, ALZ-801 or a pharmaceutically acceptable salt thereof may be administered once, twice, three, or four times daily, using any suitable mode described above. In some embodiments, ALZ-801 is administered twice a day.

Also, in certain embodiments, administration or treatment with a composition comprising tramiprosate, ALZ-801 or a pharmaceutically acceptable salt thereof may be continued for a number of weeks; for example, commonly treatment would continue for at least 2 weeks, 4 weeks, 8 weeks, 12 weeks, 16 weeks, 20 weeks, 24 weeks, 28 weeks, 32 weeks, 36 weeks, 40 weeks, 44 weeks, 48 weeks, 52 weeks, 56 weeks, 60 weeks, 64 weeks, 68 weeks, 72 weeks, 76 weeks, 80 weeks, 84 weeks, 88 weeks, 92 weeks, 96 weeks, 100 weeks, or 104 weeks. In yet further embodiments, administration or treatment with a composition comprising tramiprosate, ALZ-801 or a pharmaceutically acceptable salt thereof may be continued for a number of months; for example, commonly treatment would continue for at least 2 months, 4 months, 6 months, 8 months, 10 months, 12 months, 15 months, 18 months, 20 months, or 24 months. In still further embodiments, administration or treatment with a composition comprising tramiprosate, ALZ-801 or a pharmaceutically acceptable salt thereof may be continued indefinitely.

In certain embodiments, a composition comprising tramiprosate, ALZ-801 or a pharmaceutically acceptable salt thereof can be used in combination therapy with at least one other therapeutic agent. Tramiprosate, ALZ-801 or a pharmaceutically acceptable salt thereof and the at least one other therapeutic agent can act additively or, in certain embodiments, synergistically. In certain embodiments, a composition comprising tramiprosate, ALZ-801 or a pharmaceutically acceptable salt thereof can be administered concurrently with the administration of another therapeutic agent. In certain embodiments, a composition comprising tramiprosate, ALZ-801 or a pharmaceutically acceptable salt thereof can be administered prior or subsequent to administration of another therapeutic agent. The at least one other therapeutic agent can be effective for treating the same or different disease, disorder, or condition.

Methods of the present invention include administration of one or more compounds or pharmaceutical compositions of the present invention and one or more other therapeutic agents provided that the combined administration does not inhibit the therapeutic efficacy of the one or more compounds of the present invention and/or does not produce adverse combination effects.

In certain embodiments, compositions of the present invention can be administered concurrently with the administration of another therapeutic agent, which can be part of the same pharmaceutical composition as, or in a different composition from, that containing the compounds of the present invention. In certain embodiments, compounds of the present invention can be administered prior or subsequent to administration of another therapeutic agent. In certain embodiments of combination therapy, the combination therapy comprises alternating between administering a composition of the present invention and a composition comprising another therapeutic agent, e.g., to minimize adverse side effects associated with a particular drug. When a compound of the present invention is administered concurrently with another therapeutic agent that potentially can produce adverse side effects including, but not limited to, toxicity, the therapeutic agent can advantageously be administered at a dose that falls below the threshold at which the adverse side effect is elicited.

In certain embodiments, compounds or pharmaceutical compositions of the present invention include, or can be administered to a patient together with, another therapeutic drug that may be available over-the-counter or by prescription. U.S. patent application No. 2005/0031651 (incorporated herein by reference) provide a long but non-exhaustive list of "therapeutic drugs" that can be useful, in combination, according to the invention. Preferred therapeutic drugs to be used with the compounds or pharmaceutical compositions of the present invention are therapeutic drugs useful in the prevention or treatment of AD or its symptoms, including but not limited to donepezil (Aricept®), memantine (Namenda™), rivastigmine (Exelon™) Galanthamine (Reminyl™ and R-flurbiprofen (Flurizan™). The compounds and compositions according to the invention could also be combined with vaccines and antibodies for the prevention or treatment of AD.

It should be noted that other tramiprosate compositions or variants of tramiprosate can be administered to target the identified patient population disclosed herein. Exemplary tramiprosate compositions or variants of tramiprosate are disclosed in U.S. Pat. No. 8,748,656, the contents of which are incorporated herein by reference.

The contents of each cited application and journal article are incorporated by reference as if set forth fully herein.

EXAMPLES

Example 1

APOE4$^+$ Mild-to-Moderate Population vs. APOE4$^+$ Moderate Population

Phase 3 human clinical trials of tramiprosate to treat Alzheimer's disease at doses of 100 mg BID and 150 mg BID for up to 78 weeks were run in both North America and Europe (1691 total patients enrolled). Placebos in both trials were treatment with donepezil either alone or in combination with memantine. ADAS-Cog scores and CDR-SB scores were obtained every 13 weeks for patients that remained in the trial. The patients were genotyped for APOE4 and the severity of their disease was measured using MMSE prior to the beginning of treatment. The data from both trials were merged for certain statistical analyses. Initial statistical analyses of these data focused on APOE4 status and a statistically significant effect of both the 100 mg and 150 mg treatment groups compared with the placebo was observed for both ADAS-Cog and CDR-SB in the APOE4$^+$ subgroup.

We then performed additional subgroup analysis, subgrouping by APOE4 genotype/allele status (APOE4 heterozygous or APOE4 homozygous) and by disease severity (mild vs moderate) to determine if the number of c alleles and/or the severity of disease predicted a better outcome of tramiprosate therapy. We found that there was a better therapy outcome, as measured by a smaller increase ADAS-Cog scores and CDR-SB scores (e.g., a slower cognitive decline) in all ApoE4$^+$ patients who were characterized as having moderate severity of disease just prior to treatment.

TABLE 1

ADAS-Cog Score Change over Standard of Care for All APOE4+ Patients ≤85
Years Treated with Tramiprosate and Subgrouped by Disease Severity

| | 52 weeks (Δ improvement vs control)* | | | 65 weeks (Δ improvement vs control) | | | 78 weeks (Δ improvement vs control) | | |
|---|---|---|---|---|---|---|---|---|---|
| Disease Severity | 100 mg BID | 150 mg BID | Control | 100 mg BID | 150 mg BID | Control | 100 mg BID | 150 mg BID | Control |
| Mild-to-Moderate (MMSE 16-26) | 1.67 (n = 257) | 0.95 (n = 242) | (n = 298) | 1.82 (n = 219) | 1.23 (n = 209) | (n = 252) | 2.03 (n = 206) | 0.77 (n = 195) | (n = 228) |
| Mild (MMSE 20-26) | 0.82 (n = 171) | 0.17 (n = 164) | (n = 204) | 0.99 (n = 150) | 0.71 (n = 139) | (n = 177) | 1.3 (n = 140) | 0.27 (n = 131) | (n = 160) |
| Moderate (MMSE 16-19) | 3.45 (n = 86) | 2.52 (n = 78) | (n = 94) | 3.45 (n = 69) | 2.23 (n = 70) | (n = 75) | 3.32 (n = 66) | 1.57 (n = 64) | (n = 68) |

In Table 1, *control treatment is donepezil either alone or in combination with memantine. Positive delta values quantitate the amount by which average increase in ADAS-Cog Score points above baseline for the control group exceeded the average increase in ADAS-Cog Score points above baseline for the treatment group. Negative delta values indicate that the treatment group had a greater increase in ADAS-Cog Score over baseline than did the control group.

Figure 3:
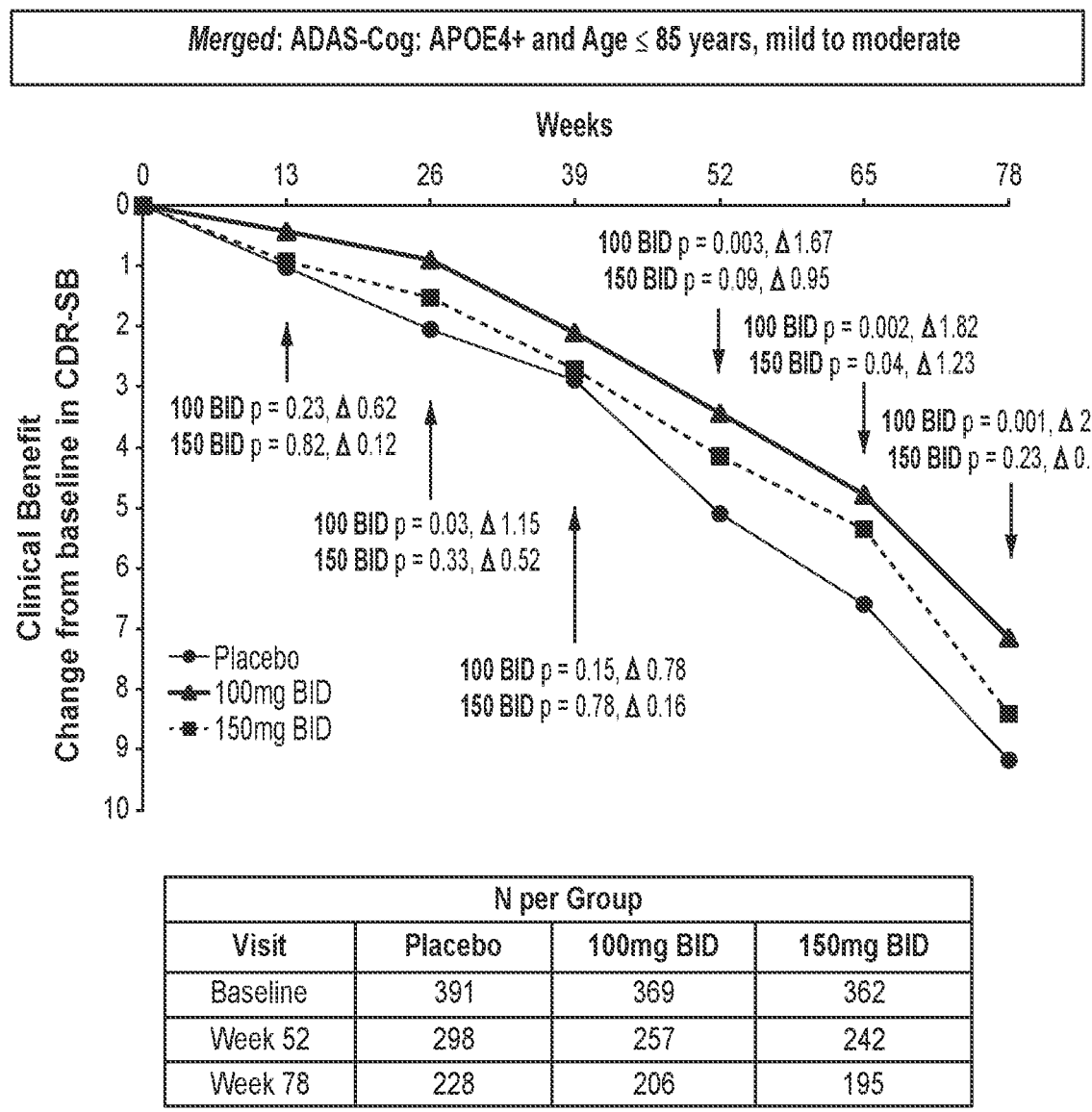
FIG. 3 demonstrates time course of tramiprosate effect (LS Mean) on ADAS-Cog in APOE4$^+$ Population at 100 mg BID and 150 mg BID (Population ≤85 Years, mild to moderate AD).
Figure 5:
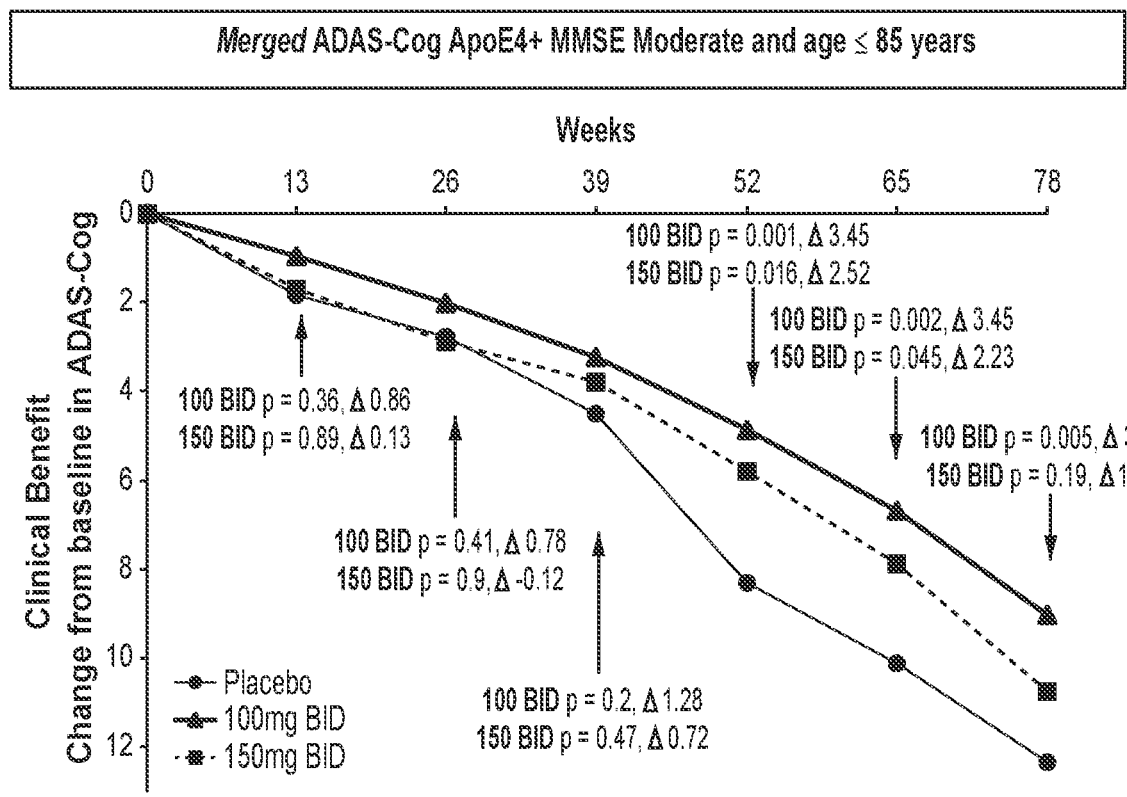
FIG. 5 demonstrates time course of tramiprosate effect (LS Mean) on ADAS-Cog in APOE4$^+$ Population at 100 mg BID and 150 mg BID (Population ≤85 Years, moderate AD).

The results demonstrate that the APOE4+ group with moderately severe AD (MMSE 16-19) showed a greater inhibition of cognitive decline as measured by ADAS-Cog than either the mildly severe AD group (MMSE 20-26) or the combined moderately and mildly severe group ("Mild-to-Moderate"; MMSE 16-26). The change in baseline ADAS-Cog score by administered dose for all APOE4+ patients without subgrouping by disease severity (i.e., the Mild-to-Moderate group) is shown in FIG. 3. The change in baseline ADAS-Cog score by administered dose for APOE4+ patients having moderate disease severity is shown in FIG. 5.

TABLE 2

CDR-SB Score Change over Standard of Care for All APOE4+ Patients ≤85
Years Treated with Tramiprosate and Subgrouped by Disease Severity

| | 52 weeks (Δ improvement vs control)* | | | 65 weeks (Δ improvement vs control) | | | 78 weeks (Δ improvement vs control) | | |
|---|---|---|---|---|---|---|---|---|---|
| Disease Severity | 100 mg BID | 150 mg BID | Control | 100 mg BID | 150 mg BID | Control | 100 mg BID | 150 mg BID | Control |
| Mild-to-Moderate (MMSE 16-26) | 0.26 (n = 254) | 0.44 (n = 243) | (n = 302) | 0.5 (n = 215) | 0.5 (n = 208) | (n = 252) | 0.55 (n = 204) | 0.6 (n = 196) | (n = 230) |
| Mild (MMSE 20-26) | 0.14 (n = 170) | 0.16 (n = 163) | (n = 206) | 0.34 (n = 147) | 0.2 (n = 138) | (n = 176) | 0.35 (n = 139) | 0.18 (n = 130) | (n = 160) |
| Moderate (MMSE 16-19) | 0.56 (n = 84) | 1.00 (n = 80) | (n = 96) | 0.83 (n = 68) | 1.12 (n = 70) | (n = 76) | 0.98 (n = 65) | 1.53 (n = 66) | (n = 70) |

In Table 2, *control treatment is donepezil either alone or in combination with memantine. Positive delta values quantitate the amount by which average increase in CDR-SB Score points above baseline for the control group exceeded the average increase in CDR-SB Score points above baseline for the treatment group. Negative delta values indicate that the treatment group had a greater increase in CDR-SB Score over baseline than did the control group.

Figure 4:
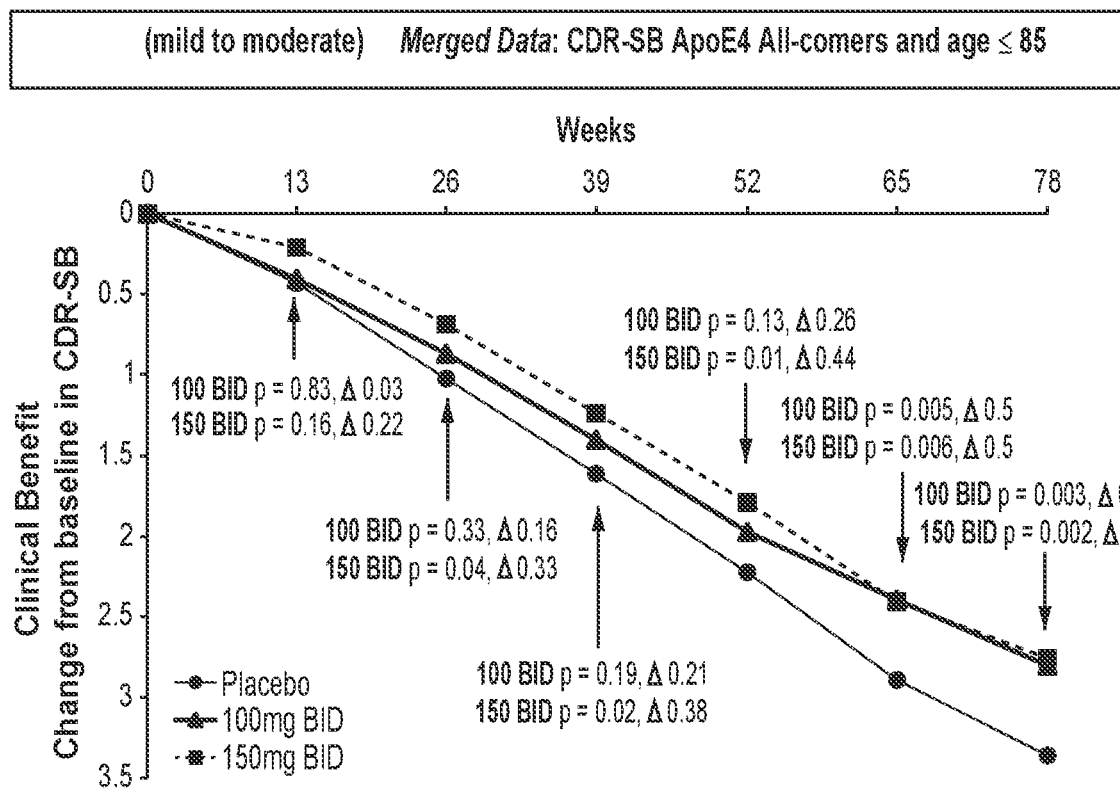
FIG. 4 demonstrates time course of tramiprosate effect (LS Mean) on CDR-SB in APOE4$^+$ Population at 100 mg BID and 150 mg BID (Population ≤Age 85 Years, mild to moderate AD).
Figure 6:
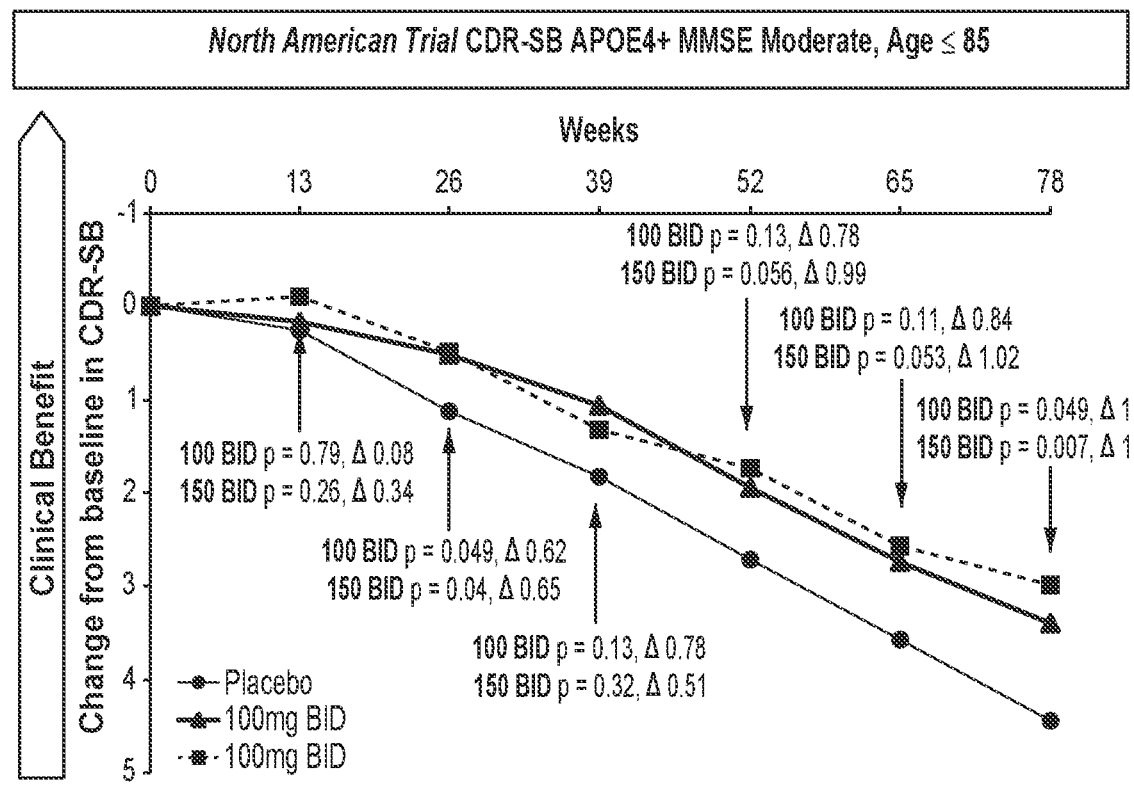
FIG. 6 demonstrates time course of tramiprosate effect (LS Mean) on CDR-SB in APOE4$^+$ Population at 100 mg BID and 150 mg BID (Population ≤85 Years, moderate AD).

The results again demonstrate that the APOE4+ group with moderately severe AD (MMSE 16-19) showed a greater inhibition of cognitive decline as measured by CDR-SB than either the mildly severe AD group (MMSE 20-26) or the combined moderately and mildly severe group ("Mild-to-Moderate'" MMSE 16-26)). The change in baseline CDR-SB score by administered dose for all APOE4+ patients without subgrouping by disease severity (i.e., the Mild-to-Moderate group) is shown in FIG. 4. The change in baseline CDR-SB score by administered dose for APOE4+ patients having moderate disease severity is shown in FIG. 6.

TABLE 3

ADAS-Cog Score Change over Standard of Care for Heterozygous APOE4+
Patients ≤85 Years Treated with Tramiprosate and Subgrouped by Disease Severity

| Disease Severity | 52 weeks (Δ improvement vs control)* | | | 65 weeks (Δ improvement vs control) | | | 78 weeks (Δ improvement vs control) | | |
|---|---|---|---|---|---|---|---|---|---|
| | 100 mg BID | 150 mg BID | Control | 100 mg BID | 150 mg BID | Control | 100 mg BID | 150 mg BID | Control |
| Mild-to-Moderate (MMSE 16-26) | 2.0 (n = 210) | 0.5 (n = 201) | (n = 233) | 0.8 (n = 187) | 0.0 (n = 174) | (n = 212) | 1.1 (n = 163) | −0.4 (n = 157) | (n = 178) |
| Mild (MMSE 20-26) | 0.9 (n = 144) | 0.1 (n = 130) | (n = 158) | −0.3 (n = 128) | −0.6 (n = 114) | (n = 146) | 0.8 (n = 114) | −0.5 (n = 102) | (n = 127) |
| Moderate (MMSE 16-19) | 4.4 (n = 66) | 1.5 (n = 71) | (n = 75) | 3.4 (n = 59) | 1.4 (n = 60) | (n = 66) | 2 (n = 49) | 0 (n = 55) | (n = 51) |

In Table 3, *control treatment is donepezil either alone or in combination with memantine. Positive delta values quantitate the amount by which average increase in ADAS-Cog Score points above baseline for the control group exceeded the average increase in ADAS-Cog Score points above baseline for the treatment group. Negative delta values indicate that the treatment group had a greater increase in ADAS-Cog Score over baseline than did the control group.

The results demonstrate that the APOE4 heterozygous group with moderately severe AD (MMSE 16-19) showed a greater inhibition of cognitive decline as measured by ADAS-Cog than either the mildly severe AD group (MMSE 20-26) or the combined moderately and mildly severe group ("Mild-to-Moderate"; MMSE 16-26). The change in baseline ADAS-Cog score by administered dose for APOE4 heterozygous patients without subgrouping by disease severity (i.e., the Mild-to-Moderate group) is shown in FIG. 1.

Figure 2:
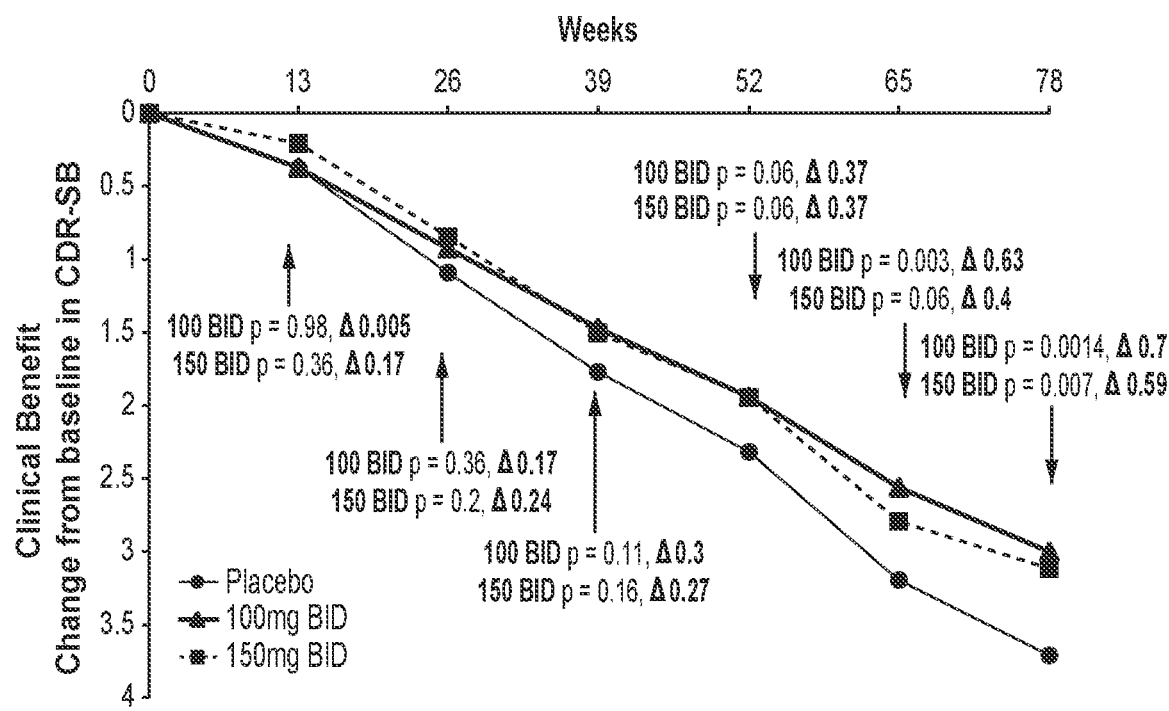
FIG. 2 demonstrates time course of tramiprosate effect (LS Mean) on CDR-SB in APOE4 Heterozygous Population at 100 mg BID and 150 mg BID (Population ≤Age 85 Years, mild to moderate AD).

SB than either the mildly severe AD group (MMSE 20-26) or the combined moderately and mildly severe group ("Mild-to-Moderate"; MMSE 16-26). The change in baseline CDR-SB score by administered dose for APOE4 heterozygous patients without subgrouping by disease severity (i.e., the Mild-to-Moderate group) is shown in FIG. 2.

Subgrouping of patients homozygous for APOE4 by disease severity was not possible due to the small number of APOE4/4 homozygous patients in the trials. Despite this, the results for all APOE4+ patients (all carriers) and APOE4 heterozygotes suggested that the superior results obtained with patients having moderately severe AD over those with mildly severe AD can be extrapolated to APOE4/4 homozygotes as well. However, further analysis of the data from the tramiprosate Phase 3 clinical trial surprisingly showed that APOE4/4 homozygotes actually responded better if they had a more mild form of the disease as shown below in Example 2.

TABLE 4

CDR-SB Score Change over Standard of Care for Heterozygous APOE4+
Patients ≤85 Years Treated with Tramiprosate and Subgrouped by Disease Severity

| Disease Severity | 52 weeks (Δ improvement vs control)* | | | 65 weeks (Δ improvement vs control) | | | 78 weeks (Δ improvement vs control) | | |
|---|---|---|---|---|---|---|---|---|---|
| | 100 mg BID | 150 mg BID | Control | 100 mg BID | 150 mg BID | Control | 100 mg BID | 150 mg BID | Control |
| Mild-to-Moderate (MMSE 16-26) | 0.5 (n = 208) | 0.4 (n = 204) | (n = 243) | 0.5 (n = 184) | 0.3 (n = 174) | (n = 217) | 0.6 (n = 161) | 0.50 (n = 161) | (n = 187) |
| Mild (MMSE 20-26) | 0.2 (n = 143) | 0.1 (n = 130) | (n = 160) | 0.3 (n = 125) | −0.1 (n = 114) | (n = 146) | 0.3 (n = 112) | 0 (n = 103) | (n = 127) |
| Moderate (MMSE 16-19) | 1.00 (n = 65) | 1.00 (n = 74) | (n = 83) | 1.00 (n = 59) | 1.1 (n = 60) | (n = 71) | 1.00 (n = 49) | 1.5 (n = 58) | (n = 60) |

In Table 4, *control treatment is donepezil either alone or in combination with memantine. Positive delta values quantitate the amount by which average increase in CDR-SB Score points above baseline for the control group exceeded the average increase in CDR-SB Score points above baseline for the treatment group. Negative delta values indicate that the treatment group had a greater increase in CDR-SB Score over baseline than did the control group.

The results demonstrate that the APOE4 heterozygous group with moderately severe AD (MMSE 16-19) showed a greater inhibition of cognitive decline as measured by CDR- Example 2

Figure 7A:
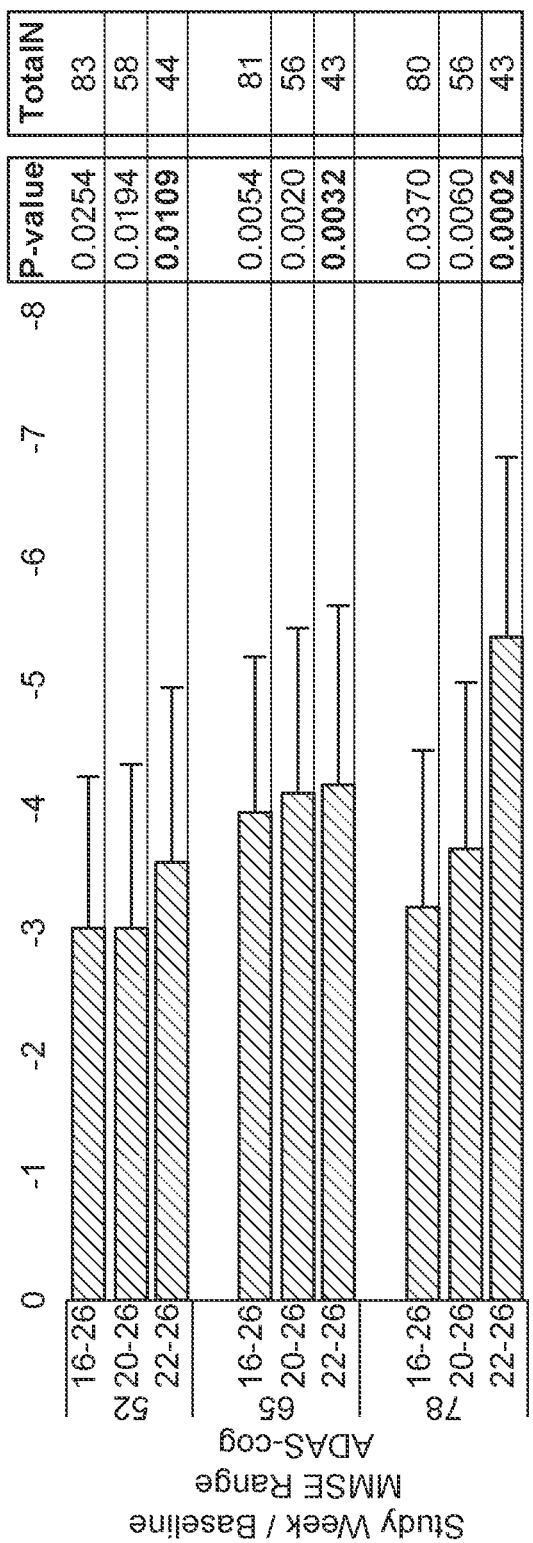
FIG. 7, panel A, demonstrates the effect of tramiprosate 150 mg BID on ADAS-Cog scores in APOE4/4 homozygous patients over 52, 65 and 78 weeks, broken down by various ranges of disease severity (as measured by baseline MMSE scores) as compared to a placebo control.
Figure 7B:
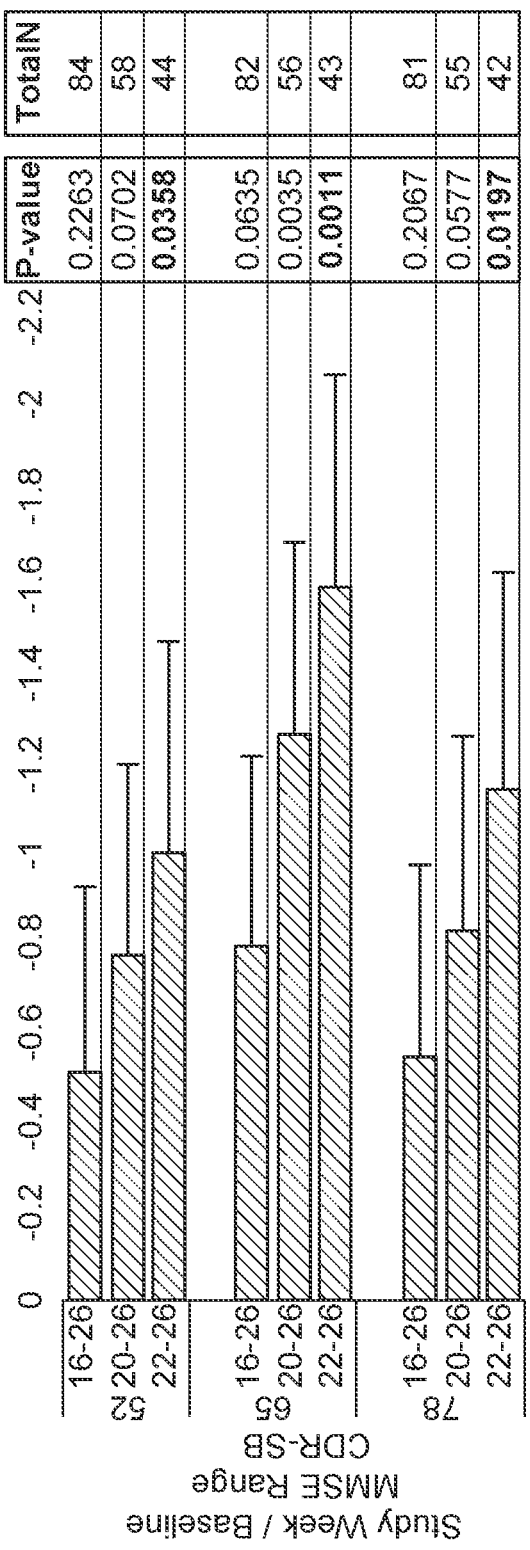

APOE4/4 Homozygous Subjects with More Mild AD Demonstrate Better Cognitive Response to Tramiprosate Analysis of the efficacy or tramiprosate in APOE4/4 homozygous subjects based on baseline MMSE was performed to evaluate for differences in drug response between Mild and Moderate patients. MMRIVI analyses were performed on the following baseline MMSE categories: Mildto-Moderate AD population (baseline MMSE 16-26 inclusive), Mild AD population (baseline MMSE 20-26 inclusive), and the More Mild AD population (baseline MMSE 22-26 inclusive). The data is shown below in FIG. 7, panels A and B.

These analyses suggest that APOE4/4 homozygous patients with Mild AD (baseline MMSE ≥20) or More Mild AD (baseline MMSE ≥22) show a higher improvement on tramiprosate at 150 mg BID than those with lower MMSE at baseline. Additionally, patients with baseline MMSE ≥22 (More Mild patients) seem to show the highest efficacy and a sustained cognitive benefit over the 78 weeks of the study. Although there were not enough subjects to analyze certain other ranges of baseline MMSE in APOE4/4 homozygous patients, the trend suggests that APOE4+ homozygous patients with mild-moderate AD (baseline MMSE=18-19) may also show a higher improvement than APOE4+ homozygous patients with more moderate AD (baseline MMSE=16-17).

Example 3

ALZ-801

To advance the clinical development of ALZ-801 into Phase 3, we have completed single dose and 14-day multiple ascending dose Phase 1 bridging studies in healthy elderly volunteers to evaluate safety, tolerability and pharmacokinetics. Compared with oral tramiprosate, a single dose of oral ALZ-801 delivered an equivalent plasma exposure of tramiprosate with over 50% lower inter-subject variability (see Table 5, below). Oral ALZ-801 also prolonged plasma tramiprosate terminal half-life to ~24 hours once steady state was achieved (see Table 6, below). The longer half-life observed in the multiple ascending dose studies was obtained after 14 days of BID dosing and was due to the fact that there were more extended blood sampling time points taken in that study as compared to the single dose study. In a multiple ascending dose study, steady state for ALZ-801 was achieved by day 7 of BID dosing and interpatient variability of both $C_{max}$ and AUC was between 24-28% at steady state.

TABLE 5

Phase I Single dose studies of ALZ-801 demonstrate improved PK profile

| Tramiprosate | ALZ-801 loose-filled capsule (N = 12) | Tramiprosate modified release tablet (N = 12) |
| --- | --- | --- |
| Cmax (ng/ml) | 628 ± 100 | 506 ± 187 |
| AUC$_{0-t}$ (h × ng/mL) | 2,680 ± 448 | 2,355 ± 747 |
| T$_{1/2}$ (h) | 14.9 ± 3.9 | 4.9 ± 2.6 |

TABLE 6

Multiple Ascending Dose Phase I studies of ALZ-801 confirm improved PK profile

| Tramiprosate | ALZ-801 loose-filled capsule (N = 12) | Tramiprosate modified release tablet (N = 12) |
| --- | --- | --- |
| Cmax (ng/ml) | 673 ± 127 [19%] | 506 ± 187 [37%] |
| AUC$_{0-t}$ (h × ng/mL) | 2,440 ± 448 [17%] | 2,355 ± 747 [32%] |
| T$_{1/2}$ (h) | 24.5 ± 3.4 [15%][1] | 4.9 ± 2.6 [53%] |

[1]Half-life was measured at 14 days based on a dose of 256.5 mg BID.

An immediate release tablet formulation of ALZ-801 was developed, which displayed exposure and low variability similar to the loose filled capsule formulation. Administration of ALZ-801 in such tablet form with food markedly reduced the incidence of GI symptoms as compared to the fasted state, while maintaining plasma tramiprosate exposure, but after a single dose of 205 mg, there was no significant difference in pharmacokinetic parameters between fed and fasted subjects. Half-life of a single dose of ALZ-801 in tablet form administered with food was determined by taking blood samples out to 24 hours post-dosing and confirmed that such half-life was approximately 24 hours. The immediate release tablet formulation displayed PK exposure and low interpatient variability similar to that observed for the loose filled capsules. ALZ-801 also showed excellent dose proportionality without accumulation or decrease in plasma exposure of tramiprosate over 14 days.

Based on the single and multiple dose pharmacokinetics of ALZ-801, the steady-state plasma exposure of the active drug tramiprosate following oral BID dosing of ALZ-801 immediate release tablet has been determined. The data indicate that between 260 and 270 mg (e.g., 265 mg) BID of ALZ-801 achieves a steady-state tramiprosate exposure that is equivalent to 150 mg BID of oral tramiprosate. These bridging data support the Phase 3 development of ALZ-801, an optimized prodrug of tramiprosate with improved GI tolerance and low inter-subject pharmacokinetic variability, in APOE4/4 homozygous AD subjects.

Figure 8:
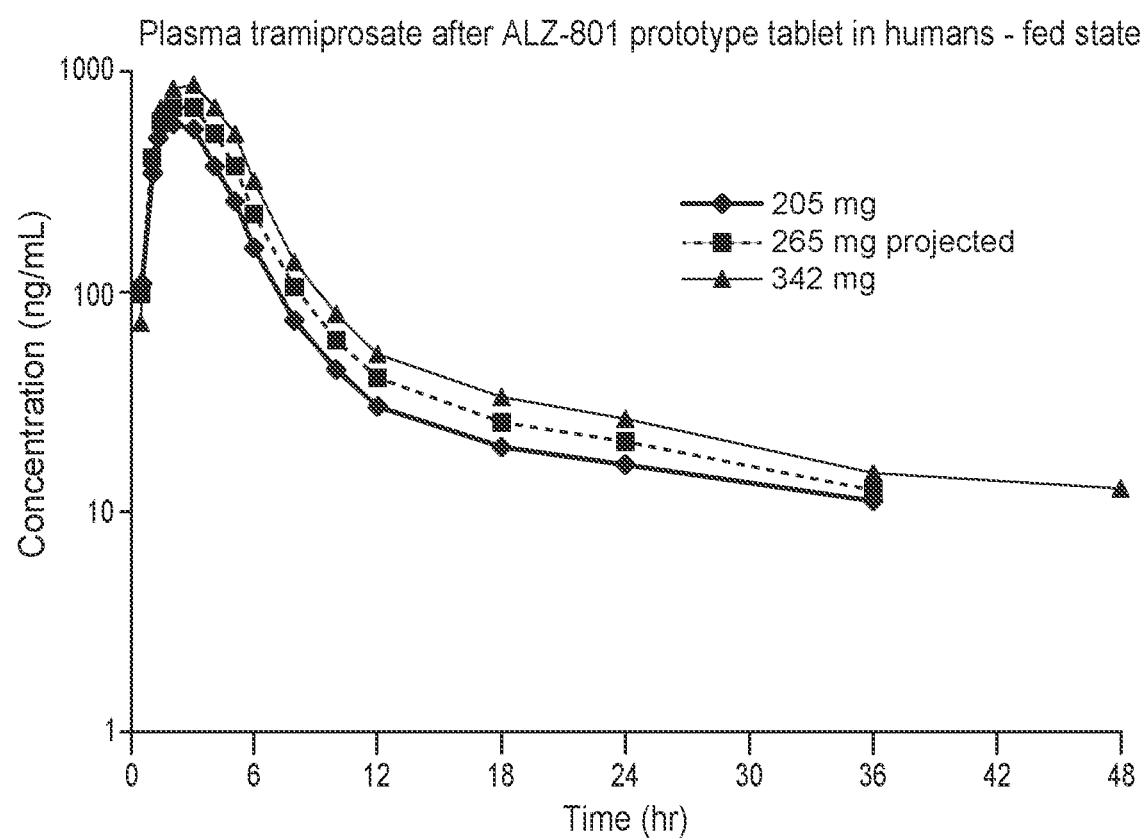
FIG. 8 depicts the time course of plasma tramiprosate levels in humans orally administered 205 mg or 342 mg of ALZ-801 in an instant release formulation, as well as the predicted time course for a 256 mg dose of ALZ-801.

Based on pharmacokinetic results from Phase I administration of 205 mg and 342 mg of ALZ-801 in an instant release oral formulation, it is predicted that a tablet or capsule comprising 265 mg of ALZ-801 in an instant release, oral formulation administered twice a day will provide a $C_{max}$ of 807 ng/ml±25%; a single dose $AUC_{12h}$ tramiprosate plasma level of 4473 ng/ml*hr±25%; and a steady state $AUC_{12h}$ tramiprosate plasma level of 4429 ng/ml*hr±25% (see FIG. 8).

The invention claimed is:

1. A method of treating Alzheimer's Disease in a subject, the method comprising administering to the subject a pharmaceutical composition comprising valyl-3-amino-1-propanesulfonic acid, or a pharmaceutically acceptable salt thereof, in an amount effective to reduce cognitive decline, only if the subject is determined to (i) be APOE4/4 homozygous; and (ii) have a baseline Mini-mental State Examination (MMSE) score of ≥22, wherein the MMSE was performed within sixty days prior to the first administration of the composition.

2. The method of claim 1, wherein the subject has more mild Alzheimer's disease as indicated by a baseline MMSE score of 22-26.

3. The method of claim 1, wherein upon administration to the subject the pharmaceutical composition delivers about 150 mg of tramiprosate/dose.

4. The method of claim 3, wherein the pharmaceutical composition comprises between 260 and 270 mg of valyl-3-amino-1-propanesulfonic acid or a pharmaceutically acceptable salt thereof.

5. The method of claim 4, wherein the composition comprises 265 mg of valyl-3-amino-1-propanesulfonic acid, and wherein the composition is formulated as an instant release, oral tablet or capsule.

6. The method of claim 1, wherein the pharmaceutical composition is administered twice daily.

7. The method of claim 1, wherein the subject is 85 years old or younger.

8. The method of claim 1, wherein the treatment decreases cognitive decline in the subject.

9. A method of determining a subject's suitability for treatment with valyl-3-amino-1-propanesulfonic acid, comprising determining the APOE4 status of the subject and the severity of the subject's Alzheimer's disease, wherein only if the subject is APOE4/4 homozygous and has a baseline Mini-mental State Examination (MMSE) score of ≥22, wherein the MMSE was performed within sixty days prior to the first administration of the composition, the subject is determined to be suitable for treatment.

10. A method of selecting and treating a patient suffering from Alzheimer's disease comprising the steps of:
(a) selecting the patient if the patient is both APOE4/4 homozygous and has a baseline Mini-mental State Examination (MMSE) score of ≥22, wherein the MMSE was performed within sixty days prior to the first administration of the composition; and
(b) administering to the selected patient a pharmaceutical composition comprising valyl-3-amino-1-propanesulfonic acid or a pharmaceutically acceptable salt thereof, in an amount effective to reduce cognitive decline.

11. A method of treating Alzheimer's Disease in a subject, the method comprising administering to the subject a pharmaceutical composition that delivers about 150 mg of tramiprosate/dose, only if the subject is determined to (i) be APOE4/4 homozygous; and (ii) have a baseline Mini-mental State Examination (MMSE) score of ≥22, wherein the MMSE was performed within sixty days prior to the first administration of the composition.

12. The method of claim 11, wherein the subject has more mild Alzheimer's disease as indicated by a baseline MMSE score of 22-26.

13. The method of claim 11, wherein the pharmaceutical composition comprises between 260 and 270 mg of valyl-3-amino-1-propanesulfonic acid or a pharmaceutically acceptable salt thereof.

14. The method of claim 13, wherein the composition comprises 265 mg of valyl-3-amino-1-propanesulfonic acid, and wherein the composition is formulated as an instant release, oral tablet or capsule.

15. The method of claim 11, wherein the pharmaceutical composition is administered twice daily.

16. A method of treating Alzheimer's Disease in a subject, the method comprising administering to the subject a pharmaceutical composition comprising between 260 and 270 mg valyl-3-amino-1-propanesulfonic acid, or a pharmaceutically acceptable salt thereof, only if the subject is determined to (i) be APOE4/4 homozygous; and (ii) have a baseline Mini-mental State Examination (MMSE) score of ≥22, wherein the MMSE was performed within sixty days prior to the first administration of the composition.

17. The method of claim 16, wherein the subject has more mild Alzheimer's disease as indicated by a baseline MMSE score of 22-26.

18. The method of claim 16, wherein the composition comprises 265 mg of valyl-3-amino-1-propanesulfonic acid, and wherein the composition is formulated as an instant release, oral tablet or capsule.

19. The method of claim 16, wherein the pharmaceutical composition is administered twice daily.

* * * * *